United States Patent [19]

Smith et al.

[11] Patent Number: 4,808,405

[45] Date of Patent: Feb. 28, 1989

[54] P-ANISOYL STREPTOKINASE/PLASMINOGEN COMPLEX

[75] Inventors: Richard A. G. Smith, Dorking; John G. Winchester, Guildford, both of England

[73] Assignee: Beecham Group p.l.c., England

[21] Appl. No.: 902,429

[22] Filed: Aug. 29, 1986

Related U.S. Application Data

[63] Continuation of Ser. No. 813,044, Dec. 24, 1985, abandoned, which is a continuation of Ser. No. 201,578, Oct. 28, 1980, abandoned.

[30] Foreign Application Priority Data

Nov. 5, 1979 [GB] United Kingdom ............... 7938279

[51] Int. Cl.$^4$ ............... A61K 37/47; A61K 37/547; C12N 11/00; C12N 9/70
[52] U.S. Cl. ............... 424/94.3; 424/94.64; 435/174; 435/188; 435/216; 514/802
[58] Field of Search ............... 435/174, 177, 188, 216, 435/217; 424/94, 94.1, 94.3, 94.64; 514/802

[56] References Cited

U.S. PATENT DOCUMENTS

| | | | |
|---|---|---|---|
| 4,082,612 | 4/1978 | Robbins et al. | 435/216 X |
| 4,178,368 | 12/1979 | Heimburger et al. | 424/94 |
| 4,285,932 | 8/1981 | Smith | 435/216 X |

OTHER PUBLICATIONS

McClintock et al., Biochemical and Biophysical Research Communications, vol. 43, No. 3, 1971, pp. 694–702.
Buck et al., J. Biol. Chem., 243, 3648–3654 (1968).
Chase, Jr. et al., Biochem., 8, 2212–2224 (1969).
McClintock et al., Biochem., 13, 5334–5344 (1974).
Markus et al., J. Biol. Chem., 251, 6495 (1976).
Brockaway et al., Biochem., 13, 2063–2069 (1974).
Abstract P5-076 0929, Thrombosis & Haemostasis, (Stuttgart), 42, 390 (1979).

*Primary Examiner*—David M. Naff
*Attorney, Agent, or Firm*—Jacobs & Jacobs

[57] ABSTRACT

A binary complex between streptokinase and plasminogen is prepared in which the catalytic site essential for fibrinolytic activity is blocked by a group which is removable by hydrolysis such that the pseudo-first order rate constant for hydrolysis of the complex is in the range $10^{-6}$ sec$^{-1}$ to $10^{-3}$ sec$^{-1}$ in isotonic aqueous media at pH 7.4 at 37° C. The complex is preferably a p-anisoyl streptokinase/plasminogen complex without internal peptide bond cleavage. The complex is useful in the treatment of venous thrombosis.

12 Claims, No Drawings

P-ANISOYL STREPTOKINASE/PLASMINOGEN COMPLEX

CROSS-REFERENCE

This is a continuation of Ser. No. 813,044 filed Dec. 24, 1985, which is a continuation of Ser. No. 201,578 filed Oct. 28, 1980, both now abandoned.

This invention relates to enzyme derivatives and in particular to derivatives of the enzyme streptokinase/-plasminogen activator complex, which derivatives are useful in the treatment of venous thrombosis.

It is known that complexes formed between streptokinase and the enzyme plasminogen may be used as thrombolytic agents in the therapeutic treatment of venous thrombosis. Plasminogen is a plasma $\beta$-globulin which is the inactive precursor of the fibrinolytic enzyme plasmin. Streptokinase is a secretory product of haemolytic streptococci and can be produced cheaply in large quantities. When streptokinase and plasminogen are mixed, there is initially formed a very strongly, but non-covalently, bound binary complex between the two. A conformational change then occurs in the plasminogen component, which uncovers a catalytic site having proteolytic activity. This catalytic site then causes peptide bond cleavages firstly in the streptokinase component and secondly in the plasminogen, which is converted to plasmin. The final complex which results when streptokinase and plasminogen are mixed, and which has been loosely termed "Streptokinase/-plasminogen complex", is therefore in fact a complex between fragmented streptokinase and plasmin. There is no method presently known to isolate the initially formed binary complex of streptokinase and plasminogen with a catalytic site before internal peptide bond cleavages occur because this labile complex immediately degrades. However, such complexes have been detected with their catalytic site blocked by mixing streptokinase and plasminogen in the presence of the acylating agent p-nitrophenyl p'-guanidinobenzoate (see D K McClintock and P H Bell, Biochem Biophys Res Comm 43, 694–702, 1979).

In European patent application No. 79301773.2 there are described fibrinolytic enzyme derivatives in which the catalytic site essential for fibrinolytic activity is blocked by a group which is removable by hydrolysis under certain conditions. One suitable fibrinolytic enzyme disclosed therein is streptokinase/plasminogen complex. As that complex is produced by first mixing the streptokinase and plasminogen and then blocking the catalytic site, the product disclosed in that patent is a blocked form of the "streptokinase/plasminogen complex", ie is a blocked form of a complex between fragmented streptokinase and plasmin.

It has now been found that a blocked derivative of the initially produced binary complex between streptokinase and plasminogen can be isolated by mixing the two in the presence of excess blocking agent, and is useful as a thrombolytic agent. Furthermore, it is more homogenous, more effective and its formation is easier to monitor than the blocked "streptokinase/plasminogen complex" disclosed in European patent application No. 79301773.2.

Accordingly the present invention provides an enzyme derivative which comprises a binary complex between streptokinase and plasminogen, which complex has the catalytic site essential for fibrinolytic activity blocked by a group which is removable by hydrolysis such that the pseudo-first order rate constant for hydrolysis of the derivative is in the range $10^{-6} \sec^{-1}$ to $10^{-3} \sec^{-1}$ in isotonic aqueous media at pH7.4 at 37° C., provided that the group which blocks the catalytic site is not the p-guanidinobenzoyl group.

As stated above, a p-guanidinobenzoyl group has been used by McClintock and Bell to acylate the initially formed complex between streptokinase and plasminogen. However the resulting blocked derivative was only formed during active-site titrations of the complex. The isolation of this derivative has not been reported. Moreover there is no suggestion in the prior art that such blocked derivatives could be used as fibrinolytic agents.

Accordingly, in a further aspect the present invention provides an isolated enzyme derivative which comprises a binary complex between streptokinase and plasminogen, which complex has the catalytic site essential for fibrinolytic activity blocked by a group which is removable by hydrolysis which that the pseudo-first order rate constant for hydrolysis of the derivative is in the range $10^{-6} \sec^{-1}$ to $10^{-3} \sec^{-1}$ in isotonic aqueous media at pH7.4 at 37° C.

The streptokinase component in the derivative of the present invention is native unfragmented streptokinase having a molecular weight of about 47,000. The previously known "streptokinase/plasminogen complex" contains fragmented streptokinase which has a molecular weight of less than 40,000.

The characteristic feature of the derivative of this invention is that, upon reduction and electrophoretic analysis in the presence of sodium dodecyl sulphate, only two polypeptide chains are detectable, one corresponding to streptokinase, molecular weight about 47,000 and the other to plasminogen. In contrast, such analysis of the previously known "streptokinase/plasminogen complex" shows at least three polypeptide components, which correspond to streptokinase fragment, having a molecular weight of less than 40,000, and the heavy and light chain of plasmin.

The plasminogen for use in preparing the derivative of this invention may be any plasminogen which forms a bimolecular complex with streptokinase, for example human, cat, dog or rabbit plasminogen. Human plasminogen is preferred.

The essential feature of the blocking group for the catalytic site of the derivative of this invention is that it should be removable by hydrolysis at a rate where the pseudo-first order rate constant for hydrolysis is not less than $10^{-6} \sec^{-1}$ and not greater than $10^{-3} \sec^{-1}$. Preferably the rate constant should be in the range $10^{-5}$ to $10^{-3} \sec^{-1}$.

Derivatives having a pseudo-first order rate constant of greater than $10^{-3} \sec^{-1}$ liberate unacceptably high levels of free enzyme before attaching to fibrin. Derivatives having pseudo-first order rate constants of less than $10^{-6} \sec^{-1}$ liberate enzyme too slowly to be of any clinical use.

The derivatives in accordance with this invention may be used as either prophylactic or therapeutic agents. For the purposes of prophylaxis a derivative having a slow rate of hydrolysis and therefore long half life is preferred. Such derivatives suitable for this purpose have pseudo-first order rate constants for hydrolysis in the range $5 \times 10^{-5}$ to $10^{-5} \sec^{-1}$ and half life of 3.5 to 16 hours. For therepeutic purposes a more rapidly hydrolysing derivative is preferred i.e. one having a pseudo-first order rate constant for hydrolysis in the range $5 \times 10^{-4}$ to $7 \times 10^{-5}$ sec$^{-1}$ which corresponds to an approximate half life of 30 minutes to 2 hours.

The pseudo-first order rate constant is determined by hydrolysing the enzyme derivative under physiological conditions i.e. in isotonic aqueous media at pH 7.4 and at 37° C. At regular intervals aliquots are withdrawn and incubated with a chromogenic or fluorogenic protease substrate such as S-2251 (H-D-Val-Leu-Lys-p-nitroanilide 2HCl) and the rate of conversion of the substrate measured.

The hydrolysis is followed until such time as the rate of conversion of substrate reaches a maximum. The rate constant k is then calculated by plotting:

$$\log_e(1 - A_t/A_{max}) \text{ against } t$$

where $A_{max}$ the maximum rate at which an aliquot converts substrate and $A_t$ is the rate at which an aliquot converts substrate at time t.

Suitable groups for blocking the catalytic site include acyl groups such as benzoyl, substituted benzoyl, acryloyl or substituted acryloyl groups. The pseudo-first order rate constant for hydrolysis of any particular substituted benzoyl enzyme derivative can be estimated on the basis of the Hammett $\sigma$ value of any substituent once the pseudo-first order rate constant of two or more substituted benzoyl derivatives have been measured provided that there is no special interaction between a particular substituent and the enzyme.

It is generally recognised that Hammett values for meta and para substituents ($\sigma_m$ and $\sigma_p$) give an acceptable prediction of hydrolysis rates. Moreover $\sigma_m$ and $\sigma_p$ values may be summed with reasonable accuracy to calculate kinetic properties of other substituted benzoyl groups bearing more than one substituent. Hammett values for ortho substituents ($\sigma_o$) cannot be summed with the same reliability as $\sigma_m$ and $\sigma_p$ values because of steric effects. However when the ortho substituent is small and therefore produces a negligible steric effect i.e. in the case of fluorine, methyl and methoxy, then the $\sigma_o$ value may within generally accepted degrees of error be used alone or summed with $\sigma_m$ and/or $\sigma_p$ values to calculate reaction rates.

Subject to these limitations, a substituted benzoyl group in which the phenyl ring bears one or more substituents, particularly meta and/or para substituents where the sum of the Hammett $\sigma$ values is in the range 0.1 to $-1.1$ is a suitable blocking group in accordance with this invention.

Suitable benzoyl and substituted benzoyl groups include benzoyl, optionally substituted with halogen, $C_{1-6}$ alkyl $C_{1-6}$ alkoxy, $C_{1-6}$ alkanoyloxy, $C_{1-6}$ alkanoylamino (RCONH—). Examples include, benzoyl, p-fluorobenzoyl, o-, m-, or p-toluoyl, o-, m-, or p-methoxybenzoyl (i.e. anisoyl), o-, m-, or p-ethoxybenzoyl, 2,4-dimethoxybenzoyl, 3,4-dimethylbenzoyl, 4-butylbenzoyl, 3-methyl-4-methoxybenzoyl, o-acetoxybenzoyl (i.e. acetylsalicyloyl) and p-acetamidobenzoyl. A further aromatic group is naphthoyl.

The exception to this general rule is where the benzoyl group contains a basic moiety such as amino, dimethylamino and guanidino. The rate of hydrolysis of such derivatives is up to ten times less rapid than the calculated value.

Another series of acyl groups which may be used in accordance with the invention are acryloyl and substituted acryloyl, in particular cinnamoyl and substituted cinnamoyl groups bearing one or more substituents particularly meta and/or para substituents in which the sum of the Hammett $\sigma$ values is in the range $-1.0$ to $+0.15$ subject to the limitations above.

Suitable substituted acryloyl groups $C_{1-6}$ alkyl-acryloyl, furyl-acryloyl, cinnamoyl, $C_{1-6}$ alkyl-cinnamoyl. Specific examples include 3,3-dimethylacryloyl, 2-furyl-3-acryloyl, cinnamoyl, and p-methylcinnamoyl.

The derivative of this invention is prepared by mixing streptokinase with plasminogen in the presence of a blocking agent which has the formula A-B or formula E-F, wherein A is a group which is selective for the catalytic site essential for fibrinolytic activity and which is capable of transferring from the group B to the catalytic site and B is a leaving group which facilitates the attachment of the enzyme by A; E is a locating group which locates the agent in the catalytic site and F is a group which is capable of transferring from the locating group to the catalytic site; and thereafter optionally isolating the derivative so formed.

The use of the agent A-B represents a direct blocking method. Agents which operate in this way are known. One example is p-nitrophenyl p'guanidinobenzoate. The guanidinobenzoyl moiety becomes selectively situated adjacent the catalytic site and its attachment is assisted by the p-nitrophenyl leaving group.

The use of the agent E-F represents an indirect blocking method. Examples of the group E include p-aminophenyl and p-acetamidinophenyl or structurally similar substituted phenyl groups containing a positively charged moiety in the meta or para position.

Examples of inverse blocking agents are: p-amidinophenyl p'fluorobenzoate, p-amidinophenyl p'-toluate, p-amidinophenyl p'anisate, p-amidinophenyl benzoate, p-amidinophenyl cinnamate, p-amidinophenyl p'-methylcinnamate, p-amidinophenyl 3-(2-furyl)-acrylate, p-amidinophenyl 2-naphthoate, p-amidinophenyl 3,3-dimethylacrylate, p-amidinophenyl 4-butyl benzoate, p-amidinophenyl 2,4-dimethoxybenzoate, p-amidinophenyl acetylsalicylate, p-amidinophenyl 4-ethoxybenzoate, p-acetamidinophenyl p'-anisate, p-amidinophenyl o-toluate, p-amidinophenyl o-anisate, p-amidinophenyl 3,4-dimethylbenzoate, p-amidinophenyl 3-methyl-4-methoxy benzoate, and p-amidinophenyl 4-acetamidobenzoate.

The direct and inverse blocking reactions are suitable carried out in aqueous buffered media at a pH range which is not detrimental to the enzyme, blocking agent or product, e.g. from pH 6 to pH 9 and preferably at approximately pH 7.

The reaction is generally carried out by mixing the blocking agent with either the streptokinase or plasminogen and then adding the other component. The molar concentration of the streptokinase should be approximately equal to that of the plasminogen. With most blocking agents the ratio of blocking agent to streptokinase employed should be at least 100 on a molar basis. Preferably a 250-fold excess is employed. With very reactive inverse or direct blocking agents, e.g. p-nitrophenyl-p'-guanidinobenzoate, a lower molar ratio may be used.

The blocking reaction should be carried out at moderate temperatures, i.e. from 0° C. to 20° C.

The time for which the reaction is allowed to proceed depends upon the blocking reagent employed, and the temperature at which the reaction is carried out. A convenient time is about 0.5 to 1 hour at 0° C. but the reaction may be allowed to continue for longer.

After the reaction is complete the derivative is purified by standard methods such as dialysis, affinity chromatography, and ultra filtration, and thereafter recovered by standard methods such as free drying from aqueous media. Where necessary the material may be adapted for example by sterilization for intravenous administration to human beings. The inverse blocking agents, E-F, where E is p-amidinophenoxy and F is an acyl group may be prepared by acylating a salt of p-hydroxybenzamidine with an acylating derivative of formula F-X, wherein F is as previously defined and X is hydroxyl or an activated derivative thereof, optionally in the presence of a catalyst.

Examples of activated acylating derivatives include the acyl chloride or bromide. These derivatives may be prepared by standard methods.

Suitable catalysts for this process include tertiary organic bases such as pyridine and condensation promoting agents such as dicyclohexylcarbodiimide.

The acylation reaction is generally carried out in a polar organic solvent which is inert to the reagents and product. Examples of suitable solvents include N,N-dimethylformamide and dimethylsulphoxide. Alternatively where the catalyst is a liquid as in the case of pyridine then the reaction may be carried out in the absence of solvent.

The reaction is generally carried out at moderate temperatures i.e. less than 70° C. and generally less than 40° C.; ambient temperature is most convenient.

The time for the reaction to proceed to completion depends upon the specific reagents employed, the solvent and the temperature at which the reaction is performed. This may be determined by following the reaction for example by thin layer chromatography.

When the reaction is complete, the product is recovered and purified by standard methods.

This invention also comprises a pharmaceutical composition which comprises a pharmaceutically acceptable carrier together with an anzyme derivative which comprises a binary complex between streptokinase and plasminogen which complex has the catalytic site essential for fibrinolytic activity blocked by a group which is removable by hydrolysis such that the pseudo-first order rate constant for hydrolysis of the derivative is in the range $10^{-6}$ sec$^{-1}$ to $10^{-3}$ sec$^{-1}$ in isotonic aqueous media at pH 7.4 at 37° C.

The compositions according to this invention are formulated in accordance with routine procedures as pharmaceutical compositions adapted for intravenous administration to human beings.

Typically compositions for intravenous administration are solutions of the sterile derivative in sterile isotonic aqueous buffer. Where necessary the composition may also include a solubility agent to keep the derivative in solution and a local anaesthetic such as lignocaine to ease pain at the site of injection. Generally, the enzyme derivative will be supplied in unit dosage form for example as a dry powder or water free concentrate in a hermetically sealed container such as an ampoule or sachette indicating the quantity of enzyme in activity units, as well as an indication of the time within which the free enzyme will be liberated. Where the derivative is to be administered by infusion, the derivative will be dispensed with an infusion bottle containing sterile pharmaceutical grade "Water for Injection". Where the derivative is to be administered by injection the derivative is dispensed with an ampoule of sterile water for injection. The injectable or infusable composition will be made up by mixing the ingredients prior to administration.

The quantity of material administered will depend upon the amount of fibrinolysis required and the speed with which it is required, the seriousness of the thromboembolic condition and the position and size of the clot. For example a patient with a pulmonory embolism or a large life threatening ascending ileo-femoral thrombus will require administration of a bolus of rapidly acting material. On the other hand where it is desired to prevent the formation of post-operative thrombi, a small quantity of slow acting material will be required. The precise dose to be employed and mode of administration may be decided according to the circumstances by the physician supervising treatment. However, in general, a patient being treated for a medium size thrombus will generally receive a daily dose of from 0.10 to 1.0 mg kg$^{-1}$ of body weight either by injection in up to eight doses or by infusion. One advantage of the derivative of this invention over previous thrombolytic agents such as streptokinase is that it can be given by injection rather than by continuous infusion, and may be administered by way of only one or two injections per day.

The following Examples illustrates the preparation of derivatives according to this invention.

Example 1

Preparation of freeze dried p-anisoyl streptokinase/plasminogen complex without internal peptide bond cleavages Streptokinase (250,000 units, Kabi, Stockholm, Sweden) was dissolved in 0.1M trishydroxymethylmethane hydrochloride pH 7.4 (2.5 ml) and a solution of 0.1M p-amidinophenyl p'-anisate in dimethylsulphoxide (0.25 ml) added. A slight cloudiness resulted. To this mixture was added 0.5 ml of a solution of human lys-plasminogen (8.99 mg/ml in the above buffer) [Kabi, Stockholm] and the solution was thoroughly and rapidly mixed. After standing on ice for 15 minutes, the solution was stored on ice until use. After approximaely 2 hours 0.4 ml (40,000 units) of the material was diluted with 3.0 ml of a slurry of L-lysine-sepharose 4B (a 33% wet wt/volume suspension in the above buffer) and stood at 0° C. for 1 hour. The gel was filtered on a glass sinter funnel at 4° C. under suction and washed with the buffer (100 ml). The gel was eluted under gentle suction with the same buffer containing 0.1M ε-aminocaproic acid (3 lots of 5 ml). The combined filtrates were dialysed for 2 hours at 4° C. against ammonium bicarbonate buffer (50 mM pH 7.0) containing 2.5% w/v mannitol. The product was then freeze dried to 0.799 g of a white solid. Approximately 195 mg of this material was analysed by slab gel polyacrylamide gel electrophoresis using 10% w/v gels in the presence of sodium dodecyl sulphate. Two main polypeptide bands were observed corresponding to lys-plasminogen (m.w. 84,000) and streptokinase (m.w. 47,000). There was also a trace of contaminating human serum albumin derived from the commercial streptokinase preparation.

Example 2

Preparation of a pharmaceutical, lyophilised composition containing p-anisoyl-(streptokinase-plasminogen) activator complex Streptokinase [45.4 ml of a 9.95 mg/ml solution in 0.03M sodium phosphate and 0.12M sodium glutamate at pH 7.5] was mixed with a lysine/mannitol buffer (110 ml) at pH 7.0 and sterile glycerol (60 ml) and stirred for 5 min. at 4° C. A sterile filtered solution of p-amidinophenyl p'anisate in DMSO (15 ml, 20 mM) was then added over 2 min and the mixture stirred for 5 min. at 4° C. Human lysplasminogen (71 ml, 11.4 mg/ml—Kabi, Stockholm) was added over 2 min and the mixture stirred for 60 min at 4° C.

Human serum albumin (clinical grade) (18.9 ml 20% w/v) was then added to the mixture and the whole stirred for 2 min, at 4° C. The volume of reaction vessel fluid was brought to 400 ml by addition of lysine/mannitol buffer. The fluid was then diafiltrated for about 2½ hours at 18° C. until 2400 ml of diafiltrate were collected. The fluid was filtered through 14 cm Millipore 0.22μ sterile filter (with a coarse prefilter) and transferred to a sterile reservoir. 5.0 ml aliquots were dispensed rapidly into sterile 20 ml freeze-drying vials (clear glass), 2-stage caps were fitted and the vials frozen on freeze drier shelves at −40° C. Freeze drying occurred over at least 24 hours and the caps were closed under sterile $N_2$ and then sealed.

The composition of each vial was as follows:
p-anisoyl-(streptokinase-plasminogen) activator complex: 4–6 mg
L-lysine.HCl: 22.8 mg
D-mannitol: 50 mg
p-amidinophenyl p'anisate: <50 μg
sodium chloride: trace

Example 3

In a similar manner to Example 1, 3-methyl, 4-methoxybenzoyl-(streptokinase-plasminogen) activator complex was prepared using p-amidinophenyl 3-methyl, 4-methoxy benzoic acid in place of p-amidinophenyl p'-anisate.

Example 4

Preparation of freeze-dried 3,5 dimethyl 4-methoxy benzoyl streptokinase/plasminogen complex without internal peptide bond cleavages Streptokinase (20 ml of a 3.58 mg/ml solution in 0.03M sodium phosphate, 0.12M sodium glutamate pH 7.5) was mixed with glycerol (20 ml) and stirred for 5 min at 40° C. p-amidinophenyl 3,5-dimethyl 4-methoxy benzoic acid. HCl (21.7 mg) in dimethylsulphoxide (3.0 ml) was added and the mixture stirred for 5 min at 4° C. Human lys-plasminogen (144 mg in 25 ml, 20 mM L-lysine. HCl, 1% w/v D-mannitol pH 7.0) was added and the mixture stirred at 4° C. for 2 hours. Human serum albumin (3 ml of a 20% w/v solution in water) was added, the mixture diluted to 250 ml with the lysine/mannitol buffer and diafiltered for 2½ hours at 4° C. when 1130 ml of diafiltrate was obtained. The residual solution was freeze-dried to give 3.018 g of a white powder which, when deacylated gave a free activator content of approximately 23.5 μg/mg.

Biological Data

The derivatives prepared according to Examples 1 to 3 were compared to the p-anisoyl derivative of the known "streptokinase/human plasminogen complex" prepared as described in Example 22 of European Patent Application No. 79301773.2, and to unmodified streptokinase-plasminogen activator complex, by systemically administering each compound to a rabbit with a radioactively labelled clot localised in its inferior vena cava. The method used was that as described in the above-mentioned European patent application, except that the thrombus is retained by a woollen thread rather than by constricting ligatures.

The mean lysis figures were determined in groups of various numbers of animals, and these results are shown in Table 1 below:

TABLE 1

| | No. of animals | Mean lysis (%) |
|---|---|---|
| 1. Controls given saline | 8 | 3 ± 1 |
| 2. Unmodified 'streptokinase-plasmonogen activator complex' prepared from equimolar quantities of both proteins at 0° C. for 10 min and injected immediately | 6 | 20 ± 4 |
| 3. Unmodified commercial streptokinase-plasminogen activator complex (Behringwerke) | 5 | 14 ± 4 |
| 4. p-anisoyl-(streptokinase-plasminogen activator complex) with internal peptide bond cleavages prepared as in example 22 of EU 79301773.2 | 5 | 24 ± 8 |
| 5. p-anisoyl-(streptokinase-plasminogen activator complex) without internal peptide bond cleavages prepared as in Example 1 | 5 | 42 ± 6 |
| 6. A pharmaceutical lyophilised preparation of p-anisoyl-(streptokinase-plasminogen activator complex) prepared as in Example 2 | 13 | 41 ± 6 |
| 7. 3-methyl, 4-methoxy-benzoyl-(streptokinase-plasminogen activator complex prepared as in Example 3 | 5 | 29 ± 5 |

These results show that, in this model, the derivatives of Examples 1 and 2 are almost twice as effective in lysing thrombi than the derivative prepared by blocking the fragmented streptokinase/plasmin complex.

In addition, Table 1 also shows that active-site acylated derivatives of streptokinase-plasminogen activator complexes are more active than their unmodified counterparts even when the unmodified complex is prepared as freshly as possible.

A second animal model was developed to test fibrinolytic agents. In this model, a thrombus was formed around an implanted woollen thread anchored in the femoral vein of a beagle dog. Blood was aspirated from the vein segment (after isolation by ligatures) via a collateral vein cannula. The aspirated blood was radiolabelled with $^{125}$I-human fibrinogen, (see European patent application No. 79301773.2) and reinjected into the evacuated vein segment together with rabbit brain thromboplastin. After clotting the ligatures were removed and the resulting radiolabelled occlusive thrombus was held in place by the thread. Table 2 below summarises the results obtained when these dogs were treated with various fibrinolytic agents. Final lysis was determined radiochemically after excision of any remaining thrombus at the end of the experiment. Table 2 shows the p-anisoyl streptokinase-plasminogen complex prepared according to the invention is significantly more active at two dose levels than the freshly prepared unmodified activator complex at the same dose levels.

Chemical data

Table 3 gives apparent first order rate constants for the deacylation of active-site substituted streptokinase-plasminogen activator complexes at 37° C./pH 7.4. The data illustrate that the deacylation rate constant is related to the electronic structure of the substituted benzoyl group. In general, electron-withdrawing substituents increase the deacylation rate and electron donating groups slow down the process.

TABLE 2

Activity of enzyme derivatives in a dog model of venous thrombosis

| | Enzyme derivative | Dose IU/kg | Number of animals | Mean lysis % |
|---|---|---|---|---|
| 1. | Controls given saline | — | 7 | 22 ± 10 |
| 2. | Unmodified 'streptokinase plasminogen activator complex prepared from equimolar quantities of both proteins at 0° C. for 10 min and injected immediately | 1500 | 5 | 10 ± 2 |
| 3. | Unmodified 'streptokinase-plasminogen activator complex prepared from equimolar quantities of both proteins at 0° C. for 10 min and injected immediately | 2500 | 5 | 25 ± 18 |
| 4. | p-anisoyl-(streptokinase plasminogen) activator complex prepared as in Example 2 | 1500 | 5 | 79 ± 14 |
| 5. | p-anisoyl-(streptokinase plasminogen) activator complex prepared as in Example 2 | 2500 | 5 | 85 ± 14 |
| 6. | Streptokinase | 1500 | 3 | 24 ± 21 |

TABLE 3

Apparent first order deacylation rate constants for active-site acylated derivatives of streptokinase-plasminogen activator complex

| Acyl group | $k_3(\sec^{-1}$ at pH 7.4, 37° C.) |
|---|---|
| Benzoyl | $3.5 \times 10^{-4}$ |
| 2-toloyl | $1.9 \times 10^{-4}$ |
| 4-anisoyl | $2.9 \times 10^{-4}$ |
| 4-fluorobenzoyl | $2.6 \times 10^{-4}$ |
| 3,methyl 4-anisoyl | $1.2 \times 10^{-4}$ |
| 3,5,dimethyl 4-anisoyl | $1.6 \times 10^{-4}$ |
| 4-nitrobenzoyl | c. $2.3 \times 10^{-2}$ |
| 4-chlorobenzoyl | $2.5 \times 10^{-3}$ |

We claim:
1. p-anisoyl streptokinase/plasminogen complex without internal peptide bond cleavage.
2. The complex of claim 1, wherein said plasminogen is human lys-plasminogen.
3. A pharmaceutical composition for the prevention and/or treatment of thromboses, which comprises a thrombolytically effective amount of a p-anisoyl streptokinase/plasminogen complex without internal peptide bond cleavage together with a pharmaceutically acceptable carrier.
4. A composition according to claim 3 in a form suitable for intravenous administration.
5. The composition of claim 3, wherein said plasminogen component of said complex is human lys-plasminogen.
6. The composition of claim 3, in the form of a lyophilized composition.
7. A method of treating venus thrombosis in a patient comprising administering to the patient a therapeutically or prophylactically effective amount of a p-anisoyl streptokinase/plasminogen complex without internal peptide bond cleavage or of a pharmaceutical composition containing the complex together with a pharmaceutically acceptable carrier.
8. A method according to claim 7 in which the daily dose for a human is from 0.10 to 1.0 mg/kg$^{-1}$ of body weight.
9. The method of claim 7, wherein said plasminogen component of said complex is human lys-plasminogen.
10. A method of treating a patient with thrombus, which comprises administering to such patient a thrombolytically effective amount of a p-anisoyl streptokinase/plasminogen complex without internal peptide bond cleavage.
11. A method according to claim 10, wherein said complex is administered by injection.
12. The method of claim 10, wherein said plasminogen component of said complex is human lys-plasminogen.

* * * * *

UNITED STATES PATENT AND TRADEMARK OFFICE
CERTIFICATE OF CORRECTION

PATENT NO. : 4,808,405
DATED : February 28, 1989
INVENTOR(S) : Richard A.G. Smith et al It is certified that error appears in the above-identified patent and that said Letters Patent is hereby corrected as shown below:

Claim 7, line 1, change "venus" to --venous--.

Signed and Sealed this

Twenty-sixth Day of September, 1989

Attest:

DONALD J. QUIGG

Attesting Officer
Commissioner of Patents and Trademarks